United States Patent
Tanimoto et al.

(10) Patent No.: US 8,415,498 B2
(45) Date of Patent: Apr. 9, 2013

(54) PROCESS FOR PRODUCING ACROLEIN AND/OR ACRYLIC ACID

(75) Inventors: Michio Tanimoto, Himeji (JP); Nobuyuki Hakozaki, Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 12/934,367

(22) PCT Filed: Mar. 11, 2009

(86) PCT No.: PCT/JP2009/055210
§ 371 (c)(1), (2), (4) Date: Sep. 24, 2010

(87) PCT Pub. No.: WO2009/125658
PCT Pub. Date: Oct. 15, 2009

(65) Prior Publication Data
US 2011/0015432 A1    Jan. 20, 2011

(30) Foreign Application Priority Data
Apr. 9, 2008    (JP) .................................. 2008-101472

(51) Int. Cl.
*C07C 51/00* (2006.01)
(52) U.S. Cl. .......................... 562/599; 562/545; 562/598
(58) Field of Classification Search .................. None
See application file for complete search history.

(56) References Cited

U.S. PATENT DOCUMENTS

| | | | |
|---|---|---|---|
| 2,451,485 A | 10/1948 | Hearne et al. | |
| 3,876,693 A | 4/1975 | Erpenbach et al. | |
| 4,014,927 A | 3/1977 | Kadowaki | |
| 4,147,885 A | 4/1979 | Shimizu et al. | |
| 4,871,700 A | 10/1989 | Uchida et al. | |
| 5,264,625 A | 11/1993 | Hammon et al. | |
| 5,442,108 A | 8/1995 | Kawajiri et al. | |
| 7,022,877 B2 | 4/2006 | Dieterle et al. | |
| 7,154,009 B2 | 12/2006 | Dieterle et al. | |
| 7,211,692 B2 | 5/2007 | Dieterle et al. | |
| 7,612,007 B2 | 11/2009 | Miura et al. | |
| 2004/0015013 A1 | 1/2004 | Hammon et al. | |
| 2006/0135346 A1 | 6/2006 | Nakamura et al. | |
| 2009/0088316 A1 | 4/2009 | Nakamura et al. | |

FOREIGN PATENT DOCUMENTS

| | | |
|---|---|---|
| GB | 1 473 035 | 5/1977 |
| JP | 49-76810 | 7/1974 |
| JP | 49-132007 | 12/1974 |
| JP | 50-12410 | 5/1975 |
| JP | 50-151816 | 12/1975 |
| JP | 52-108917 | 9/1977 |
| JP | 63-137755 | 6/1988 |
| JP | 5-229984 | 9/1993 |
| JP | 6-262081 | 9/1994 |
| JP | 2005-95874 | 4/2005 |
| JP | 2005-272313 | 10/2005 |
| JP | 2007-509864 | 4/2007 |
| JP | 2007-509867 | 4/2007 |
| JP | 2007-509884 | 4/2007 |
| JP | 2008-6359 | 1/2008 |

OTHER PUBLICATIONS

International Search Report issued May 19, 2009 in corresponding International (PCT) Application No. PCT/JP2009/055210 (of record).
International Preliminary Report on Patentability together with English translation of Written Opinion issued Nov. 30, 2010 in corresponding International (PCT) Application No. PCT/JP2009/055210.
Yoshiro Ogata, "Oxidation and Reduction of Organic Compound," Nankodo Co., Ltd., Nov. 1, 1963, pp. 141-142 (with English translation).
Supplementary European Search Report issued May 2, 2012 in corresponding European Application No. 09730500.7.

*Primary Examiner* — Sudhakar Katakam
(74) *Attorney, Agent, or Firm* — Wenderoth, Lind & Ponack, L.L.P.

(57) ABSTRACT

In industrial scale production of acrolen and/or acrylic acid by catalytic gas-phase oxidation of propylene or a propylene-containing gas with molecular oxygen or a molecular oxygen-containing gas or in industrial scale production of acrylic acid by catalytic gas-phase oxidation of acrolein or an acrolein-containing gas with molecular oxygen or a molecular oxygen-containing gas, this invention provides a process characterized in that the initial stage operation is carried out under advancedly elevated reaction temperature and thereafter the reaction temperature is lowered to carry out the steady state operation. According to this process, acrolein and/or acrylic acid can be produced in high yield stably over prolonged period.

8 Claims, No Drawings

PROCESS FOR PRODUCING ACROLEIN AND/OR ACRYLIC ACID

TECHNICAL FIELD

This invention relates to a process for producing acrolein and/or acrylic acid by catalytic gas-phase oxidation of propylene or a propylene-containing gas with molecular oxygen or a molecular oxygen-containing gas, or an improvement in a process for producing acrylic acid by catalytic gas-phase oxidation of acrolein or an acrolein-containing gas, with molecular oxygen or a molecular oxygen-containing gas.

BACKGROUND ART

Acrylic acid is industrially important as a starting material for various synthetic resins, paints, plasticizing agents and the like. In recent years, importance of acrylic acid particularly as a starting material of water absorbent resins gathers weight and the demand therefore tends to increase.

For production of acrylic acid, new processes such as catalytic vapor-phase oxidation of the acrolein which is obtained through dehydration of glycerin from natural sources have been proposed in recent years. However, two-stage catalytic gas-phase oxidation comprising producing acrolein by catalytic gas-phase oxidation of propylene, and producing acrylic acid by catalytic gas-phase oxidation of the resulting acrolein is the most generally used process, which has been widely and industrially worked. Concerning such production process of acrylic acid by two-stage gas-phase catalytic oxidation of propylene, a number of companies have offered various proposals aiming at acrylic acid production in a higher yield stably over a longer period.

For example, Patent Document 1 (U.S. 2004/0015013A1) discloses a process wherein a part of the deteriorated catalyst during the catalytic vapor-phase oxidation is replaced with fresh catalyst, to produce the object product stably over a longer period, without changing the whole catalyst layer. Also Patent Document 2 (JP 2005-95874A) discloses a process wherein the deteriorated catalyst is once discharged from the fixed bed reactor, regenerated, and re-loaded. Patent Documents 3 (JP 6341988)-137755A), 4 (JP 6(1994)-262081A), 5 (JP 2007-509884T), 6 (JP 2007-509864T), 7 (JP 2007-509867T) and 8 (JP 2008-6359A) disclose the processes comprising suspending the reaction temporarily and passing a specific gas through the catalyst layer(s) to regenerate the deteriorated catalyst.

Acrylic acid is currently produced on a scale of several millions of tons per year in the whole world, and the demand therefore has been increasing in recent years particularly as a starting material of water absorbent resins. Still in addition, price of its starting gas is rising drastically. Under the circumstances, even a little improvement (e.g., by 0.1%) in the yield on industrial scale production of acrylic acid will bring a very significant economical merit. While all of the above-enumerated known processes achieve certain improvements in respect of acrylic acid yield or longer operation period as intended, they still leave room for improvement viewed from industrial scale production. For example, the partial catalyst exchange or catalyst regeneration as proposed in the cited patent documents can extend the catalyst life, but require temporary suspension of the reaction during which the production amount of acrylic acid decreases. Thus, economically the processes are not yet fully satisfactory.

This led us to the thought, if a novel process to control the reduction in catalytic activity itself during the reaction could be found, it would enable to extend the duration of the usable period of the catalyst without suspending the reaction, and to enable continuous operation over a prolonged period. Still in addition, we thought that the usable period of the catalyst would be further extended if such a novel process is adopted in combination with the known regeneration treatment as referred to in the above.

Accordingly, therefore, the object of the present invention lies in continuous production of acrolein and/or acrylic acid in high yields over a longer period, by applying such a novel process to industrial scale catalytic gas-phase oxidation of propylene or a propylene-containing gas with molecular oxygen or a molecular oxygen-containing gas, or to industrial scale catalytic gas-phase oxidation of acrolein or an acrolein-containing gas with molecular oxygen or a molecular oxygen-containing gas.

DISCLOSURE OF THE INVENTION

We have engaged in concentrative research work with the view to accomplish the above object, to make a surprising discovery that reduction in the catalytic activity during the steady-state operation could be suppressed by running the initial stage operation at a temperature higher than that in the steady state operation, in advance of the steady state operation at the prescribed temperature, against the generally accepted view that a high temperature reaction is disadvantageous to catalyst life. In conventional gas-phase oxidation reactions, the oxidation is performed, by elevating the reaction temperature as the catalyst deteriorates with time, from the start-up (feeding of a starting gas) stage, whereby maintaining the catalytic activity. By contrast, in the present invention the catalyst layer disposed at the gas-inlet site is positively and temporarily exposed to high temperatures at the start-up stage of the gas-phase oxidation reaction whereby to activate the catalyst with high efficiency, and thereafter the reaction temperature is lowered to carry out the steady state operation. In said process, the catalyst exhibits high performance from the beginning of the steady state operation and the high catalytic activity is maintained continuously over a long period.

Thus, according to the present invention, it is made possible to control the reduction in catalytic performance with time and to produce the object product continuously in high yield over a long period, in the production of acrolen and/or acrylic acid by catalytic gas-phase oxidation of propylene or a propylene-containing gas with molecular oxygen or a molecular oxygen-containing gas; or in the production of acrylic acid by catalytic gas-phase oxidation of acrolein or an acrolein-containing gas with molecular oxygen or a molecular oxygen-containing gas; in particular, in the production of acrylic acid by two-stage catalytic gas-phase oxidation of propylene or a propylene-containing gas with molecular oxygen or a molecular oxygen-containing gas.

Hereinafter the present invention is explained in detail referring to its preferred working embodiments, it being understood that the scope of the invention is not restricted by the explanations, and the exemplary embodiments given hereafter can be suitably modified within a range not impairing the purpose of the invention in working them.

According to the invention, in the occasion of catalytic gas-phase oxidation on an industrial scale, the initial stage operation is run from the start-up under a reaction temperature advancedly elevated higher than that for steady state operation, and thereafter the reaction temperature is lowered for running the steady state operation. This enables activation of the catalyst disposed at the gas-inlet site with high efficiency, which results in high performance of the catalyst at the gas-inlet site and suppression of its deterioration during the subsequent steady state operation under the lowered temperature, leading to production of the object product stably in a high yield over a long period. More specifically, for example, the term during which the conversion of the starting material such as propylene or acrolein is maintained at the target level can be extended when, for example, the steady state operation is carried out under a constant reaction temperature. Whereas, when the steady state operation is run under gradually or stagewisely elevated reaction temperature to maintain a prescribed conversion of the starting material, the temperature rise rate can be slowed down, leading to an extension of the period for the reaction temperature to reach the upper limit as set in the process.

The reaction temperature which is advancedly elevated higher than that for the steady state operation is, while affected by such factors as the scale or construction of the reactor, or kind of catalyst or its loading model to a certain extent, normally within a range of 300° C.-350° C. in case of producing acrolein and acrylic acid by catalytic gas-phase oxidation of propylene or a propylene-containing gas with molecular oxygen or a molecular oxygen-containing gas. Whereas, in case of producing acrylic acid by catalytic gas-phase oxidation of acrolein or an acrolein-containing gas with molecular oxygen or a molecular oxygen-containing gas, it is normally within a range of 250° C.-300° C. Where necessary, it is allowable to supply the starting gas at the reaction temperature for the steady state operation in the occasion of start-up, but for effecting the catalyst activation at a high-efficiency, it is necessary to perform the initial stage operation at the reaction temperature which is raised at the earliest possible stage.

In the present invention, it is preferred to carry out the initial stage operation at a temperature higher than the prescribed temperature for the steady state operation by 2-20° C., in particular, by 3-15° C., for activating the catalyst at a high efficiency. Where the initial stage operation is carried out under a reaction temperature higher than the prescribed temperature for the steady state operation by less than 2° C., the catalyst activation effect is not sufficiently exhibited. Conversely, even when the initial stage reaction is carried out under a temperature high enough for the catalyst activation, if the subsequent steady state operation is run without lowering the temperature by 2° C. or more (i.e., if the steady state operation is not run under the optimum reaction temperature range), drastic yield drop is invited due to degradation in the catalyst's performance and its thermal deterioration caused by over-oxidation. On the other hand, when the initial stage operation is run under a temperature higher than the prescribed temperature for the steady state operation by more than 20° C. (i.e., when the initial stage operation is not run under the optimum reaction temperature range), thermal deterioration of the catalyst takes place due to the over-oxidation reaction, resulting in yield drop or, in the worst case, in loss of catalytic activity. After the steady state operation, if necessary the reaction may be run under a temperature higher than that used in the initial stage operation. For example, where the steady state operation is run while elevating the reaction temperature so as to maintain the prescribed conversion as aforesaid, the upper limit temperature at the final stage may be set up above the reaction temperature used in the initial stage operation, and the operation may be continued until the reaction temperature reaches the upper limit.

Duration of the initial stage operation according to the invention is not particularly limited because it varies depending on the kind of used catalyst or its loading model. Normally it is suitably selected from the range of 24 hours to 1000 hours from the initiation of the starting gas supply. When it is less than 24 hours, catalyst's activation becomes insufficient. Conversely, when it exceeds 1000 hours, thermal deterioration of the catalyst takes place due to its prolonged exposure to the high temperature.

The catalysts useful for the present invention are subject to no particular limitation and any known, conventional oxide catalyst for catalytic gas-phase oxidation can be used. For example, as the catalyst for production of acrolein and acrylic acid by catalytic gas-phase oxidation of propylene or a propylene-containing gas with molecular oxygen or a molecular oxygen-containing gas, an oxide catalyst comprising the active ingredients represented by the following formula (1) is preferred:

$$Mo_{12}Bi_aFe_bA_cB_dC_eD_fO_x \qquad (1)$$

(wherein Mo is molybdenum, Bi is bismuth, Fe is iron, A is at least one element selected from the group consisting of cobalt and nickel, B is at least one element selected from the group consisting of alkali metals, alkaline earth metals and thallium, C is at least one element selected from the group consisting of tungsten, silicon, aluminum, zirconium and titanium, D is at least one element selected from the group consisting of phosphorus, tellurium, antimony, tin, cerium, lead, niobium, manganese, arsenic and zinc, O is oxygen, and a, b, c, d, e, f and x respectively denote atomic ratios of Bi, Fe, A, B, C, D and O wherein $0<a\leqq10$, $0<b\leqq20$, $2\leqq c\leqq20$, $0<d\leqq10$, $0\leqq e\leqq30$, $0\leqq f\leqq4$ and x is a value determined according to the state of oxidation of each of the elements).

Also as the catalyst for production of acrylic acid by catalytic gas-phase oxidation of acrolein or an acrolein-containing gas with molecular oxygen or a molecular oxygen-containing gas, an oxide catalyst comprising the active ingredients represented by the following formula (2) is preferred:

$$Mo_{12}V_gW_hCu_iE_jF_kG_lH_mO_y \qquad (2)$$

(wherein Mo is molybdenum, V is vanadium, W is tungsten, Cu is copper, E is at least one element selected from the group consisting of cobalt, nickel, iron, lead and bismuth, F is at least one element selected from the group consisting of antimony, niobium and tin, G is at least one element selected from the group consisting of silicon, aluminum, titanium and zirconium, H is at least one element selected from alkali metals, O is oxygen, and g, h, i, j, k, l, m and y respectively denote atomic ratios of V, W, Cu, E, F, G, H and O wherein $2\leqq g\leqq15$, $0\leqq h\leqq10$, $0<i\leqq6$, $0\leqq j\leqq30$, $0\leqq k\leqq6$, $0\leqq l\leqq60$, $0\leqq m\leqq6$, and y is a numerical value determined according to the state of oxidation of each of the elements).

There is no particular limitation also as to the shape of the catalyst, which may be spherical, columnar, ring-formed or amorphous. Obviously, spherical shape does not mean true spheres but substantially spherical shape is satisfactory. This applies also to columnar and ring forms. The molding method again is subject to no particular limitation, and any of well known methods such as extrusion molding, tabletting and so on for molding the active ingredients into a fixed shape; or having an optional inert carrier having a fixed shape carry the active ingredients, can be used.

It is unnecessary to use each a single catalyst in loading a reactor. For example, plural kinds of catalysts differing in activity may be loaded by the order of their activity levels, or a part of the catalyst(s) may be diluted with an inert carrier.

As the reactor for use, tube type, in particular, shell-and-tube type, reactor is preferred, in which each one reaction tube has an inner diameter ranging normally 15-50 mm, preferably 20-40 mm, in particular, 22-38 mm.

In the present invention, the reaction conditions are subject to no particular limitation so long as they conform to the purpose of the invention, and those conditions generally adopted in acrolein and/or acrylic acid production by catalytic gas-phase oxidation of propylene or a propylene-containing gas with molecular oxygen or a molecular oxygen-containing gas, or those adopted in acrylic acid production by catalytic gas-phase oxidation of acrolein or an acrolein-containing gas with molecular oxygen or a molecular oxygen-containing gas, can be applied. For example, in the reaction for producing acrolein from propylene, a gaseous mixture (the starting gas) of 1-15 vol %, preferably 4-12 vol %, of propylene; 0.5-25 vol %, preferably 2-20 vol % of molecular oxygen; 0-30 vol %, preferably 0-25 vol % of steam and the balance of an inert gas such as nitrogen, is contacted with an oxidation catalyst at a temperature range of 280-450° C. under a reaction pressure ranging 0.1-1.0 MPa at a space velocity of 300-5,000 $h^{-1}$ (STP).

Similarly, in the reaction for producing acrylic acid from acrolein, a gaseous mixture of 1-15 vol %, preferably 4-12 vol %, of acrolein; 0.5-25 vol %, preferably 2-20 vol % of molecular oxygen; 0-30 vol %, preferably 0-25 vol % of steam and the balance of an inert gas such as nitrogen is contacted with an oxidation catalyst at a temperature range of 230-400° C., under the reaction pressure ranging 0.1-1.0 MPa at a space velocity of 300-5,000 $h^{-1}$ (STP).

Needless to say, as the acrolein-containing gas, the one obtained by the above-described catalytic gas-phase oxidation of propylene can be used. For catalytic gas-phase oxidation of propylene, known methods such as the one using a first reactor loaded with a catalyst(s) for propylene oxidation and a second reactor loaded with a catalyst(s) for acrolein oxidation, in which the reaction gas containing acrolein supplied from the first reactor is introduced into the second reactor together with a recycle gas, oxygen or an inert gas such as nitrogen or steam, to produce acrylic acid by oxidizing the acrolein; or the one using a single reactor having two reaction zones one of which is loaded with a catalyst(s) for propylene oxidation and the other, with a catalyst(s) for acrolein oxidation, to produce acrylic acid from propylene, can be used. It should be noted that the reaction temperature as referred to in this application substantially corresponds to the heating medium inlet temperature in the reactor or reaction zone, and the heating medium inlet temperatures are determined in accordance with each of the prescribed temperature selected from the aforesaid respective temperature ranges.

In production of acrolein or acrylic acid on an industrial scale, normally the amount of the catalyst loaded in a gas-phase oxidation reactor reaches several to several tens of tons. On the other hand, normal production rate of a catalyst is at the most in the order of hundreds kgs per time, and plural lots of the catalyst has to be produced to obtain the necessary amount. This gives rise to a possibility that catalytic activity differs among the production lots, some failing to reach the intended catalytic performance level or in extreme cases being rejected as a substandard product. When the process of this invention is applied to such a situation, even the low performance catalyst lot not reaching the intended level or the lot which would conventionally be rejected can be activated to the prescribed performance level with high efficiency and used for the catalytic gas-phase oxidation reaction. This invention thus is very meritorious also from such an economical standpoint.

An acrolein-containing gas or acrylic acid-containing gas as obtained from the catalytic gas-phase oxidation are collected as an acrolein-containing solution or acrylic acid-containing solution by such known means as absorption with water or a high temperature-boiling hydrophobic organic solvent or direct condensation. Purifying the obtained solutions by per se known extraction, distillation or crystallization method, purified acrolein or purified acrylic acid can be obtained.

Industrial Utility

Thus obtained pure acrylic acid is conveniently used for producing water absorbent resin following a method known per se. For example, a water absorbent resin can be obtained by crosslinking polymerization of a monomer mixture containing the pure acrylic acid and/or a salt thereof as its chief component (preferably no less than 70 mol %, in particular, no less than 90 mol %) using about 0.001-5 mol % (based on the acrylic acid) of a crosslinking agent and about 0.001-2 mol % of a radical polymerization initiator, and subsequent drying and pulverization of the resulting polymer. A water absorbent resin is a water-swellable and water-insoluble polyacrylic acid having a crosslinked structure which absorbs at least 3 times, preferably 10-1000 times, its own weight of pure water or physiological saline to form a water-insoluble hydrogel containing not more than 25 mass %, preferably not more than 10 mass %, of water-soluble component. Examples of such water absorbent resins or methods for their property measurements are disclosed, for example, in U.S. Pat. Nos. 6,107,358, 6,174,978, 6,241,928 and so on.

BEST EMBODIMENTS FOR WORKING THE INVENTION

Hereinafter the present invention is concretely explained, referring to non-limitative examples. In the descriptions hereunder, "mass part" is written simply as "part" for convenience. Conversion and yield are respectively defined as follows:

conversion (mol %)=(mol number of reacted starting material/mol number of supplied starting material)×100 yield (mol %)=(mol number of produced object product/mol number of supplied starting material)× 100.

Example 1

Preparation of the Catalyst

In 2200 parts of distilled water, 350 parts of ammonium molybdate was dissolved under heating and stirring (solution A). Separately, 207 parts of cobalt nitrate and 86.5 parts of nickel nitrate were dissolved in 600 parts of distilled water (solution B). Also separately, 73.4 parts of ferric nitrate and 104 parts of bismuth nitrate were dissolved in an acidic solution formed by adding 25 parts of conc. nitric acid (65 mass %) to 350 parts of distilled water (solution C). These nitrate solutions (solutions B and C) were added to solution A dropwise, and successively 1.34 parts of potassium nitrate was added. Further adding 24.1 parts of antimony trioxide and 42.1 parts of alumina, a suspension was obtained. The resulting suspension was evaporated to dryness under heating and stirring to form a solid cake, which was dried at 200° C. and pulverized to not greater than 150 μm in size to provide a catalyst powder. Into a tumbling granulator 1350 parts of spherical a-alumina carrier of 4.0 mm in average particle diameter was added, and into which the catalyst powder together with a 35 mass % aqueous ammonium nitrate solution as the binder were slowly fed to have the carrier support the catalyst, followed by 6 hours' heat treatment at 480° C. in an atmosphere of air to provide catalyst 1. The composition of the metal elements in this catalyst excepting the carrier and oxygen was as follows:

$$Mo_{12}Bi_{1.3}Co_{4.3}Ni_{1.8}Fe_{1.1}K_{0.1}Sb_{1.0}Al_{5.0.}$$

The supported rate of the catalyst 1 as calculated by the following equation was about 30 mass %.

Supported rate (mass %)=(mass of supported catalyst powder (g)/mass of the carrier used (g))×100

Catalyst 2 was prepared similarly to the catalyst 1 except that spherical alumina carrier of 7.0 mm in average particle diameter was used. The supported rate of catalyst 2 was about 30 mass %.

[Reactor]

A reactor composed of a SUS reaction tube of 3000 mm in total length and 25 mm in inner diameter, and a shell for passing a heating medium therethrough and for covering the reaction tube was set vertically. From the top of the reaction tube the catalyst 2 and catalyst 1 were successively dropped to load the reaction tube, the respective catalyst layer lengths being 900 mm and 2,000 mm.

[Oxidation]

The temperature of the heating medium (the reaction temperature) was maintained at 330° C., and into the catalyst-loaded reaction tube a gaseous mixture of 7.3 vol % of propylene, 13 vol % of oxygen, 20 vol % of steam and the balance of an inert gas such as nitrogen was supplied from the bottom of the reaction tube at a space velocity of 1650 hr$^{-1}$ (STP), to carry out oxidation of the propylene. After 300 hours of the operation, the heating medium temperature was lowered to 312° C., and the reaction was continued until 8,000 hours while controlling the heating medium temperature so as to maintain the conversion at 98%. The result after the 8,000 hours' operation was as shown in Table 1.

Comparative Example 1

Example 1 was repeated except that the reaction was continued for 8,000 hours without lowering the heating medium temperature after introducing the starting material gas at 330° C. The result after the 8000 hours' operation was as shown in Table 1. The conversion was 99% for the 1,000 hours from the introduction of the starting gas, but thereafter started to drop rapidly. In order to maintain the conversion of 98%, it was necessary to gradually elevate the reaction temperature, which had to be elevated to 349° C. after passing of 8,000 hours. The result after 8,000 hours' operation indicated, as in Table 1, that much combustion reaction took place and the yields of the object products acrolein and acrylic acid were low.

TABLE 1

| | Performance After 8,000 Hours | | |
|---|---|---|---|
| | Reaction Temp. (° C.) | Propylene Conversion (mol %) | Acrolein + Acrylic Acid Yield (mol %) |
| Example 1 | 327 | 98.0 | 94.0 |
| Comparative Example 1 | 349 | 98.0 | 90.2 |

Example 2

Preparation of the Catalyst

In 3000 parts of distilled water, 500 parts of ammonium paramolybdate, 82.8 parts of ammonium metavanadate and 95.6 parts of ammonium paratungstate were dissolved under heating and stirring. Separately, 85.5 parts of copper nitrate and 41.2 parts of cobalt nitrate were dissolved in 300 parts of water under heating and stirring. The resulting two aqueous solutions were mixed, and to which 27.5 parts of antimony trioxide and 24.5 parts of titanium dioxide were added to form a suspension. The suspension was heated under stirring and evaporated, and the resulting evaporation residue was dried at 240° C., followed by pulverization to not greater than 150 µm is size to provide a catalyst powder. Into a centrifugal flow coating apparatus, 1605 parts of spherical silica-alumina carrier of 5.0 mm in average particle diameter was added, and then the catalyst powder together with 20 mass % aqueous glycerin solution as the binder were slowly fed into the apparatus, as being passed through a hot air flow of 90° C., to have the carrier support the catalyst. The supported catalyst was heat-treated at 410° C. for 6 hours in an atmosphere of air, to provide catalyst 3. The supported rate of this catalyst 3 was about 32 mass %, and the composition of the metal elements in this catalyst excepting the oxygen and carrier was as follows:

$$Mo_{12}V_3W_{1.5}Sb_{0.8}Co_{0.6}Cu_{1.5}Ti_{1.3}.$$

Catalyst 4 was prepared similarly to the catalyst 3, except that spherical silica-alumina carrier of 8.0 mm in average particle diameter was used. The supported ratio of catalyst 4 was about 32 mass %.

[Reactor]

A reactor composed of a SUS reaction tube of 3000 mm in total length and 25 mm in inner diameter, and a shell for passing a heating medium therethrough and for covering the reaction tube was set vertically. From the top of the reaction tube the catalyst 4 and catalyst 3 were successively dropped to load the reaction tube, the respective catalyst layer lengths being 700 mm and 2,200 mm.

[Oxidation]

The temperature of the heating medium (the reaction temperature) was maintained at 276° C., and into the catalyst-loaded reaction tube a gaseous mixture of 7.0 vol % of acrolein, 8.2 vol % of oxygen, 25 vol % of steam and the balance of an inert gas such as nitrogen was supplied from the bottom of the reaction tube at a space velocity of 1700 hr$^{-1}$ (STP), to carry out oxidation of the acrolein. After 500 hours of the operation, the heating medium temperature was lowered to 265° C. to initiate the steady state operation which was continued until 8000 hours in total operation time was attained, while controlling the heating medium temperature so as to maintain the conversion at 98%. The result after the 8,000 hours' operation was as shown in Table 2.

Comparative Example 2

Example 2 was repeated except that the heating medium temperature was maintained at 265° C. from the introduction time of the starting gas and the reaction was continued for 8,000 hours without the start-up stage operation at 276° C. The result after the 8,000 hours' operation was as shown in Table 2. In order to maintain the acrolein conversion of 98%, it was necessary to elevate the reaction temperature to 271° C. as early as 500 hours after initiation of the operation and after 8,000 hours, it had to be elevated to 282° C. As shown in Table 2, the result after the 8,000 hours' operation was a low yield, due to the insufficient catalyst activation at the inlet part.

TABLE 2

| | Performance After 8,000 Hours | | |
|---|---|---|---|
| | Reaction Temp. (° C.) | Acrolein Conversion (mol %) | Acrylic Acid Yield (mol %) |
| Example 2 | 273 | 98.0 | 94.1 |
| Comparative Example 2 | 282 | 98.0 | 93.7 |

Example 3

Reactor

Into a fixed bed shell-and-tube type reactor composed of approximately 9,500 reaction tubes (each having an inner diameter of 25 mm and a length of 6,000 mm) and a shell for passing a heating medium therethrough and for covering the reaction tubes, catalyst 2, catalyst 1, SUS Raschig rings each having an outer diameter of 8 mm, catalyst 4 and catalyst 3 were dropped from the top of each of the reaction tubes by the order stated, making the lengths of respective layers as follows: catalyst 2, 900 mm; catalyst 1, 2,000 mm; Raschig rings, 200 mm, catalyst 4, 700 mm; and catalyst 3, 2,200 mm. A 50 mm-thick partition plate to divide the shell into the upper and lower parts was installed at the position 3,000 mm from the bottom of the shell, and in both of the upper and lower shell spaces a heating medium was circulated upwards from the lower part. Hereafter the reaction zone loaded with catalysts 1 and 2 is referred to as the first reaction zone, and the reaction zone loaded with catalysts 3 and 4, as the second reaction zone.
[Oxidation]
The reaction temperature at the first reaction zone was set at 324° C. and that at the second reaction zone was set at 275° C. A gaseous mixture of 8 vol % of propylene, 15 vol % of oxygen, 12 vol % of steam and the balance of an inert gas such as nitrogen was introduced from a lower part of the reactor at a space velocity to the catalysts loaded in the first reaction zone of 1600 h$^{-1}$ (STP). After 600 hours passed, the reaction temperature in the first reaction zone was lowered to 313° C., and that in the second reaction zone was lowered to 266° C. to carry out the steady state operation. At that time, the propylene conversion was 98.0 mol % and the acrylic acid yield was 88.6 mol %. The reaction was continued until 8,000 hours while controlling the heating medium temperature so as to maintain the propylene conversion at 98%. After 8,000 hours, the reaction temperature at the first reaction zone was 322° C., that at the second reaction zone was 273° C., propylene conversion was 98.0 mol % and acrylic acid yield was 88.4 mol %.

The invention claimed is:
1. A process for producing acrolein and/or acrylic acid, which comprises:
conducting a catalytic gas-phase oxidation of a gas with molecular oxygen or a molecular oxygen-containing gas to obtain an acrolein and/or acrylic acid product, wherein an initial operation of the catalytic gas-phase oxidation is carried out under a first reaction temperature, and thereafter, a steady state operation of the catalytic gas-phase oxidation is carried out at a second reaction temperature that is lower than the first reaction temperature, and
wherein,
when the gas is propylene or a propylene-containing gas, the product is acrolein and/or acrylic acid and the catalytic gas-phase oxidation of the gas is carried out in the presence of an oxide catalyst comprising an active ingredient represented by the following formula (1):

$$Mo_{12}Bi_aFe_bA_cB_dC_eD_fO_x \qquad (1)$$

wherein Mo is molybdenum, Bi is bismuth, Fe is iron, A is at least one element selected from the group consisting of colbalt and nickel, B is at least one element selected from the group consisting of alkali metals, alkaline earth metal and thallium, C is at least one element selected from the group consisting of tungsten, silicon, aluminum, zirconium and titanium, D is at least one element selected from the group consisting of phosphorus, tellurium, antimony, tin, cerium, lead, niobium, manganese, arsenic and zinc, O is oxygen, and a, b, c, d, e, f and x respectively denote atomic ratios of Bi, Fe, A, B, C, D and O wherein 0<a≦10, 0<b≦20, 2≦c≦20, 0<d≦10, 0≦e≦30, 0≦f≦4, and x is a value determined according to a state of oxidation of each element,
and when the gas is acrolein or an acrolein-containing gas, the product is acrylic acid and the catalytic gas-phase oxidation of the gas is carried out in the presence of an oxide catalyst comprising an active ingredient represented by the following formula (2):

$$Mo_{12}V_gW_hCu_iE_jF_kG_lH_mO_y \qquad (2)$$

wherein Mo is molybdenum, V is vanadium, W is tungsten, Cu is copper, E is at least one element selected form the group consisting of colbalt, nickel, iron, lead and bismuth, F is at least one element selected from the group consisting of antimony, niobium and tin, G is at least one element selected from the group consisting of silicon, aluminum, titanium and zirconium, H is at least one element selected from alkali metals, O is oxygen, and g, h, i, j, k, l, m and y respectively denote atomic ratios of V, W, Cu, E, F, G, H and O wherein 2≦g≦15, 0≦h≦10, 0<i≦6, 0≦j≦30, 0≦k≦6, 0≦l≦60, 0≦m≦6, and y is a numerical value determined according to a state of oxidation of each element.
2. The process according to claim 1, wherein the product is acrylic acid, which is produced by a two-stage catalytic gas-phase oxidation of propylene or a propylene-containing gas with molecular oxygen or a molecular oxygen-containing gas.
3. The process according to claim 1, wherein the first reaction temperature is higher than the second reaction temperature by 2 to 20° C.
4. The process according to claim 1, wherein the initial operation is carried out for 24 to 1,000 hours from initiation of a gas supply.
5. The process according to claim 2, wherein the first reaction temperature is higher than the second reaction temperature by 2 to 20° C.
6. The process according to claim 2, wherein the initial operation is carried out for 24 to 1,000 hours from initiation of a gas supply.
7. The process according to claim 3, wherein the initial operation is carried out for 24 to 1,000 hours from initiation of a gas supply.
8. The process according to claim 5, wherein the initial operation is carried out for 24 to 1,000 hours from initiation of a gas supply.

* * * * *